US009299269B2

(12) United States Patent
Midathala (10) Patent No.: US 9,299,269 B2
(45) Date of Patent: Mar. 29, 2016

(54) SYSTEM FOR EVALUATING DRIVING COMPETENCY OF A SUBJECT

(76) Inventor: Ravikumar Midathala, Hyderabad (IN)

( * ) Notice: Subject to any disclaimer, the term of this patent is extended or adjusted under 35 U.S.C. 154(b) by 255 days.

(21) Appl. No.: 14/000,618

(22) PCT Filed: Feb. 17, 2012

(86) PCT No.: PCT/IN2012/000111
§ 371 (c)(1),
(2), (4) Date: Aug. 21, 2013

(87) PCT Pub. No.: WO2012/114351
PCT Pub. Date: Aug. 30, 2012

(65) Prior Publication Data
US 2013/0330691 A1    Dec. 12, 2013

(30) Foreign Application Priority Data
Feb. 21, 2011   (IN) .............................. 487/CHE/2011

(51) Int. Cl.
*G09B 19/16* (2006.01)
*A61B 5/18* (2006.01)
*A61B 3/028* (2006.01)
*A61B 3/06* (2006.01)

(52) U.S. Cl.
CPC ............... *G09B 19/167* (2013.01); *A61B 5/18* (2013.01); *A61B 3/028* (2013.01); *A61B 3/06* (2013.01)

(58) Field of Classification Search
CPC ..................................................... G09B 19/167
USPC ............................................................ 434/62
See application file for complete search history.

(56) References Cited

U.S. PATENT DOCUMENTS 4,057,911 A * 11/1977 Sack ............................. 434/64
2006/0195018 A1 * 8/2006 Guillen ........................ 600/300

* cited by examiner

*Primary Examiner* — Xuan Thai
*Assistant Examiner* — Robert P Bullington
(74) *Attorney, Agent, or Firm* — James M. Smedley LLC; James Michael Smedley, Esq.

(57) ABSTRACT

A system for testing and evaluating driving competency of a subject is disclosed. The system includes a first test unit for providing a simple driving reaction test sequence, a complex driving reaction test sequence and a depth perception test sequence, a second test unit for providing a low illumination vision test sequence and a glare recovery test sequence, a third test unit for providing a side vision test sequence, a first switching module for enabling the subject to undergo the simple driving reaction test sequence and the complex driving reaction test sequence, a second switching module for enabling the subject to undergo the depth perception test sequence, the low illumination vision test sequence, and the glare recovery test sequence, a master control unit for interacting and controlling the first test unit, the second test unit, the third test unit, the first switching module, and the second switching module.

11 Claims, 6 Drawing Sheets

SYSTEM FOR EVALUATING DRIVING COMPETENCY OF A SUBJECT

CROSS-REFERENCE TO RELATED APPLICATIONS

This application claims the benefit to PCT application number PCT/IN2012/0001111, filed Feb. 17, 2012 which is hereby incorporated by reference in its entirety. The aforementioned PCT application further claims priority to India Patent Application number 487/CHE/2011, filed Feb. 21, 2011, which is also hereby incorporated by reference in its entirety.

TECHNICAL FIELD

The invention pertains to a testing device in general. More particularly the present invention pertains to a system for testing and evaluating driving competency of a subject.

BACKGROUND

The enormous increase in street and highway traffic results in equal increase in number of accidents day by day. These accidents result in vulnerable material loss and human loss in terms of life or permanent invalidism. The safety of traffic on the highways and streets depends on the fact that the proper reaction of the driver and the control of speed in a given hazardous traffic situation. In addition to some acquired information, training and possession of driving competence, the driver is also required to possess a particular psycho-physiological competence, considering the dynamics of the driven vehicle, the human life and health hazards connected therewith.

Currently, the tests conducted for verifying the competency of the driver while operating a vehicle are generally limited to a written test, a summary vision test and a road test. As a matter of understanding, the written test evaluates one's knowledge of the regulation and the established "rules-of-the-road". Conventional vision tests for verifying the competency of the drivers are typically limited to verifying the driver's static acuity and depth perception. When applicable, the road tests are used to check the driver's basic competence in handling the vehicle while the driver is driving and using the established conventions while operating the vehicle in the traffic.

Conventionally, devices for monitoring the alertness of the driver by administering successive stimuli and analyzing the driver responses to the administered stimuli are known. Typically, the accuracy of the responses involves the evaluation of correct responses, errors of commission when a response is given at the wrong time and errors of omission when a response is not given at all. Such devices include discrimination level tests characterized in that the driver needs to respond to the presence or the absence of a stimulus in the form of an audible signal or a visual signal. Disadvantages of such discrimination level tests include that the stimulus can be of such intensity so as to cause a sudden change in the state of alertness of the driver, thereby disguising the driver true state of alertness. The discrimination level detected by the driver depends on the environment in which the test is performed.

Typically, the defects commonly observed among the drivers meeting with accidents on the highways and streets are lack of alertness, inadequate depth perception, poor peripheral, night vision and inability to recover quickly from glare effects. It is therefore recognized that driver requires higher order of alertness, depth perception ability, good peripheral and night vision, and ability to recover quickly from glare effect while operating the vehicle on the highways and streets.

In light of the aforementioned discussion, there clearly exists a need of a system for testing and evaluating driving competency of a subject by measuring the psycho-physiological characteristics, the situational awareness capabilities and that would assist to overcome or at least substantially ameliorate the disadvantages and shortcomings of the conventional systems.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In accordance with teachings of the present disclosure, a system for testing and evaluating driving competency of a subject is disclosed.

In accordance with the further teachings, the present invention contemplates an improved system for testing and evaluating driving competency of the subject and that resolves the above referenced difficulties and others.

The principal object of the present invention is to provide the system that would assist in evaluating the competency of the subject in terms of the defects commonly observed among the subjects meeting with accidents on the highways and streets.

It is a further object of the invention to provide testing means which would enable an automatic evaluation of driving competency of the subject when multiple testing units are being used and controlled by a single master control unit.

It is still a further object of the invention to provide a device which objectively measures competency of the subject to drive a vehicle in a variable environment and situations in a reliable and efficient manner.

Accordingly, another objective of the present invention is to facilitate a user to evaluate alertness level associated with the subject, depth perception ability of the subject, peripheral and night vision of the subject, and ability of the subject to recover from glare effect without the exposure of the subject to the risk of on-road testing.

In accordance with an aspect of the present invention, a system for testing and evaluating driving competency of a subject includes at least one first test unit for providing a plurality of first driving test sequences to the subject, whereby the plurality of first driving test sequences including a simple driving reaction test sequence, a complex driving reaction test sequence, and a depth perception test sequence.

In accordance with the aspect of the present invention, the system for testing and evaluating driving competency of the subject includes at least one second test unit for providing a plurality of second driving test sequences to the subject, whereby the plurality of second driving test sequences including a low illumination vision test sequence, and a glare recovery test sequence.

In accordance with the aspect of the present invention, the system for testing and evaluating driving competency of the subject includes at least one third test unit for providing a third driving test sequence to the subject, whereby the third driving test sequence including a side vision test sequence.

In accordance with the aspect of the present invention, the system for testing and evaluating driving competency of the subject includes at least one first switching module in communication with the at least one first test unit for enabling the subject to undergo the plurality of first driving test sequences.

In accordance with the aspect of the present invention, the system for testing and evaluating driving competency of the subject includes at least one second switching module in communication with the at least one first test unit and the at least one second test unit for enabling the subject to undergo the first driving test sequence, and the second driving test sequence.

In accordance with the aspect of the present invention, the system for testing and evaluating driving competency of the subject includes at least one master control unit for interacting and controlling the first test unit, the second test unit, the third test unit, the first switching module, and the second switching module.

In accordance with the aspect of the present invention, the at least one master control unit, the at least one first test unit, the at least one second test unit, the at least one third test unit, the at least one first switching module, the at least one second switching module are capable of being programmed for displaying, measuring, and recording a plurality of test parameters associated with testing and evaluating driving competency of the subject.

BRIEF DESCRIPTION OF THE DRAWINGS

Other objects and many of the attendant advantages of the invention are readily appreciated as the same becomes better understood by reference to the following detailed description when considered in connection with the accompanying drawing wherein.

DETAILED DESCRIPTION

Reference will now be made in detail to the described embodiment of the invention, so as to enable a person skilled in the art to make and use the invention in the context of a particular application, namely that of testing and evaluating the driving competency of a subject without the exposure of the subject to the risk of on-road testing. It is understood that this example is not intended to limit the invention to one preferred embodiment or application. On the contrary, it is intended to cover alternatives, modifications, and equivalents. Various modifications to the present invention will be readily apparent to a person skilled in the art, and can be made to the described embodiment within the spirit and scope of the invention as defined by the appended claims.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item.

For a better understanding, components of the described embodiment are labeled with three digit component numbers. In general, the same first digit is used throughout the entire component numbers numbered and labeled within a figure except for FIG. 1. Like components are designated by like reference numerals throughout the various figures.

Exemplary embodiments of the present invention are directed towards a system for testing and evaluating driving competency of a subject. In accordance with an aspect of the present invention, the system for testing and evaluating driving competency of the subject includes at least one first test unit for providing a plurality of first driving test sequences to the subject, whereby the plurality of first driving test sequences including a simple driving reaction test sequence, a complex driving reaction test sequence, and a depth perception test sequence. The simple driving reaction test sequence and the complex driving reaction test sequence evaluates and determines an alertness level of the subject with respect to a response time taken by the subject. The response time not exceeding 0.37 seconds qualifies the subject in the simple driving reaction test sequence. The response time not exceeding 0.67 seconds qualifies the subject in the complex driving reaction test sequence. The depth perception test sequence evaluates and determines competency of the subject with respect to a difference of distance between a first column of a plurality of lighting means corresponding to a first lighting panel and a second column of the plurality of lighting means corresponding to a second lighting panel. The difference of distance not exceeding 75 mm qualifies the subject in the depth perception test sequence. The at least one first test unit includes a plurality of light indicators for presenting the simple driving reaction test sequence and the complex reaction test sequence to the subject, and a perception window comprising the first lighting panel and the second lighting panel configured on either side for presenting the depth perception test sequence to the subject.

According to the aspect of the present invention, the system for testing and evaluating driving competency of the subject includes at least one second test unit for providing a plurality of second driving test sequences to the subject, whereby the plurality of second driving test sequences including a low illumination vision test sequence, and a glare recovery test sequence. The low illumination vision test sequence evaluates and determines competency of the subject in recognizing a plurality of traffic symbols under a low level of illumination with respect to the response time taken by the subject. The response time not exceeding 7 seconds qualifies the subject in the low illumination vision test sequence. The glare recovery test sequence evaluates and determines competency of the subject in recovering from a glare effect from the approaching vehicle with respect to the response time taken by the subject. The response time not exceeding 8 seconds qualifies the subject in the glare recovery test sequence. The at least one second test unit further comprising a plurality of headlamps for presenting the glare recovery test sequence to the subject.

According to the aspect of the present invention, the system for testing and evaluating driving competency of the subject includes at least one third test unit for providing a third driving test sequence to the subject, whereby the third driving test sequence including a side vision test sequence. The side vision test sequence evaluates and determines the competency of the subject with respect to a visualization angle subtended by the subject's eyes on either side of a path. The visualization angle equal to or exceeding 150 degrees qualifies the subject in the side vision test sequence. The at least one third test unit includes a plurality of lighting panels configured on either edges of a platform for presenting the side vision test sequence to the subject, a plurality of switches on either side of the platform for generating a wave motion on either side of eyes, and a predefined location for placing chin of the subject on the center of the platform.

In accordance with the aspect of the present invention, the system for testing and evaluating driving competency of the subject includes at least one first switching module in communication with the at least one first test unit for enabling the subject to undergo the plurality of first driving test sequences. The at least one first switching module comprising a plurality of switching elements for enabling the subject to convey the response corresponding to the simple driving reaction test sequence and the complex driving reaction test sequence.

In accordance with the aspect of the present invention, the system for testing and evaluating driving competency of the subject includes at least one second switching module in communication with the at least one first test unit and the at least one second test unit for enabling the subject to undergo the first driving test sequence, and the second driving test sequence. The at least one second switching module includes a plurality of first switching elements for enabling the subject to respond to the low illumination vision test sequence; and the glare recovery test sequence, and a plurality of second switching elements for enabling the subject to respond to the depth perception test sequence.

According to the aspect of the present invention, the system for testing and evaluating driving competency of the subject includes at least one master control unit for interacting and controlling the first test unit, the second test unit, the third test unit, the first switching module, and the second switching module. The at least one master control unit includes a test selector means for selecting the first driving test sequence, the second driving test sequence and the third driving test sequence, a display means for displaying a name and a result corresponding to the first driving test sequence, the second driving test sequence and the third driving test sequence, a plurality of buttons for performing an initiation and a termination of the first driving test sequence, the second driving test sequence and the third driving test sequence, and a plurality of indicating means for indicating a result, an initiation and a termination of the first driving test sequence, the second driving test sequence, and the third driving test sequence.

According to the aspect of the present invention, the at least one master control unit, the at least one first test unit, the at least one second test unit, the at least one third test unit, the at least one first switching module, the at least one second switching module are capable of being programmed for displaying, measuring, and recording a plurality of test parameters associated with testing and evaluating driving competency of the subject.

The master control unit capable of being configured as an application platform in the form of a user interface on a communication device preferably including a personal computer, a laptop, and a PDA, communicatively coupled with the first test unit, the second test unit, and the third test unit. The application platform, in the form of user interface on the communication device enables an instructor to conduct the predefined test sequences for the subject, monitor and evaluate the results of the predefined test sequences instantly with greater ease and with a provision for generating and printing a test report associated with the subject.

In accordance with the aspect of the present invention, the system for testing and evaluating driving competency of the subject further includes a timer means to record the response time taken by the subject.

Figure 1:
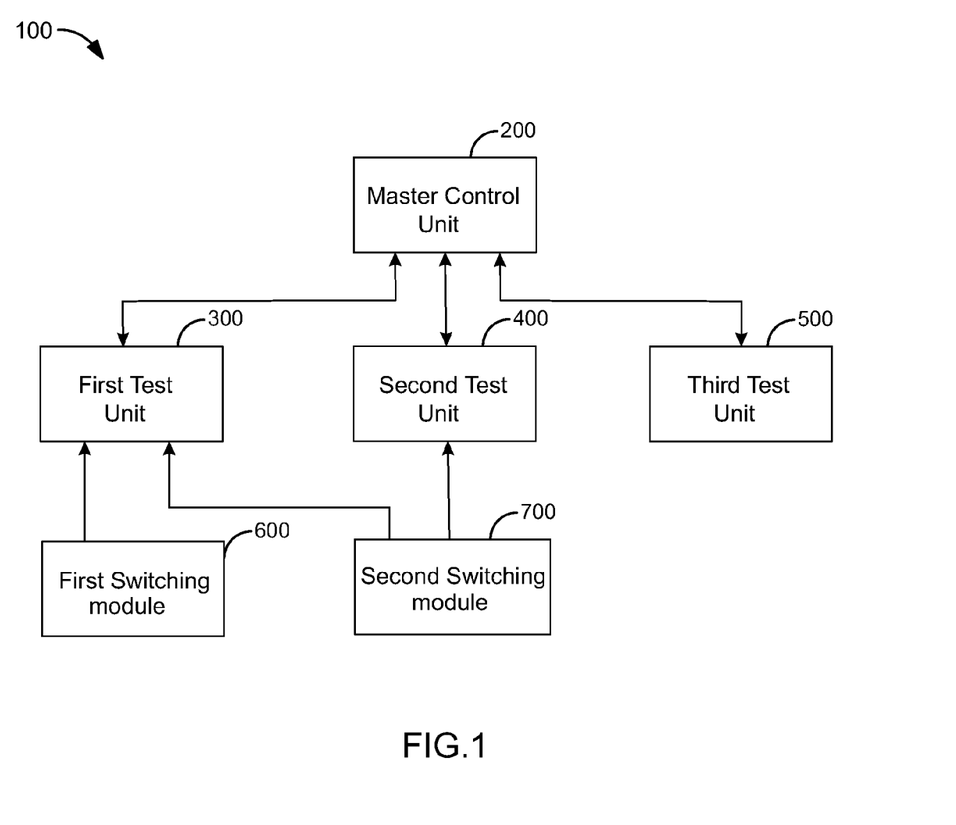
FIG. 1 is a block diagram depicting an overview of a system configured for testing and evaluating driving competency of a subject.

Referring to FIG. 1, is a diagram 100 depicting an overview of a system configured for testing and evaluating driving competency of a subject. In accordance with a non-limiting exemplary embodiment of the present invention, the system configured for testing and evaluating driving competency of the subject includes a first test unit 300, a second test unit 400, a third test unit 500, a first switching module 600, and a second switching module 700 in communication with a master control unit 200.

In accordance with a non-limiting exemplary embodiment of the present invention, the first test unit 300 provides multiple driving test sequences including a simple driving reaction test sequence, a complex driving reaction test sequence, and a depth perception test sequence. The simple driving reaction test sequence and the complex driving reaction test sequence basically evaluate and determine an alertness level associated with the subject with respect to a response time taken by the subject. The response time taken by the subject not exceeding 0.37 seconds and 0.67 seconds are considered to be qualifying response time for the simple driving reaction test sequence and the complex driving reaction test sequence respectively. The depth perception test sequence basically evaluates and determine driving competency of the subject with respect to a difference of distance evaluated between a column of multiple lighting means corresponding to a lighting panel and a column of the multiple lighting means corresponding to another lighting panel situated in a depth perception window of the first test unit 300. The difference of distance not exceeding 75 mm is considered to be qualifying difference in the depth perception test sequence.

In accordance with a non-limiting exemplary embodiment of the present invention, the second test unit 400 provides multiple driving test sequences including a low illumination vision test sequence, and a glare recovery test sequence. The low illumination vision test sequence tests and determines competency of the subject in recognizing multiple traffic symbols under a low level of illumination with respect to the response time taken by the subject. The response time not exceeding 7 seconds is considered to be qualifying response time for the subject while the subject is exposed to the low illumination vision test sequence. The glare recovery test sequence tests and determines the capability of the subject to recover from a glare effect caused by an approaching vehicle with respect to the response time taken by the subject. The response time not exceeding 8 seconds is considered to be qualifying response time for the subject while the subject is exposed to the glare recovery test sequence.

In accordance with a non-limiting exemplary embodiment of the present invention, the third test unit 500 provides a side vision test sequence which tests and determines the competency of the subject with respect to a visualization angle subtended by the subject's eyes on either side of a path. The visualization angle made by both the eyes equal to or exceeding 150 degrees is considered to qualifying visualization angle in the side vision test sequence.

According to a non-limiting exemplary embodiment of the present invention, the first switching module 600 in communication with the first test unit 300 enables the subject to undergo the simple reaction test sequence and the complex reaction test sequence presented by the first test unit 300. The first switching module 600 includes multiple buttons corresponding to accelerator and brake for enabling the subject to respond to the simple reaction test sequence and the complex reaction test sequence.

In accordance with a non-limiting exemplary embodiment of the present invention, the second switching module 700 in communication with the first test unit 300 and the second test unit 400 enables the subject to undergo the depth perception test sequence presented by the first test unit 300, the low illumination test sequence and the glare recovery test sequence presented by the second test unit 400. The second switching module 700 includes a first set of buttons assisting the subject to take up the depth perception test sequence and a second set of buttons corresponding to multiple traffic symbols for assisting the subject to take up the low illumination test sequence and the glare recovery test sequence.

According to a non-limiting exemplary embodiment of the present invention, the master control unit 200 for communicating and controlling the first test unit 300, the second test unit 400, the third test unit 500, the first switching module 600, and the second switching module 700 acts as an input and output device.

Figure 2:
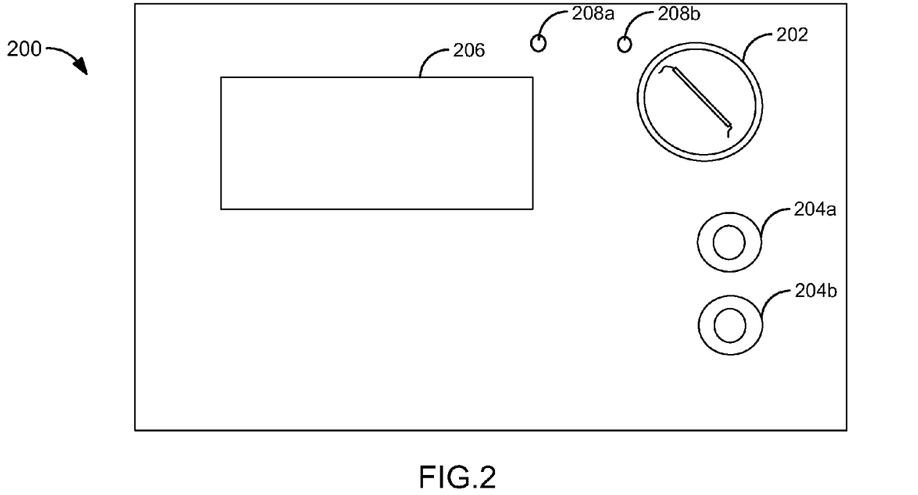
FIG. 2 is a diagram depicting a master control unit constructed in accordance with this invention.

Referring to FIG. 2 is a diagram 200 depicting a master control unit constructed in accordance with this invention. The master control unit 200 includes a test selector means 202, multiple buttons 204a and 204b, a display means 206, and multiple indicating means 208a, 208b.

According to a non-limiting exemplary embodiment of the present invention, the test selector means 202 preferably includes but limited to multiple test selector switches, a test selector knob and the like. The test selector means 202 having a six knob positions assists in presenting multiple test sequences to the subject. Each knob position corresponds to a predefined test sequence. In the context of the present invention a first knob position is allotted the simple reaction test sequence, a second knob position is allotted the complex reaction test sequence, a third knob position is allotted the depth perception test sequence, a fourth knob position is allotted the low illumination test sequence, a fifth knob position is allotted the glare recovery test sequence, and the sixth knob position is allotted the side vision test sequence, however the modifications in assigning the knob positions with multiple test sequence is equally possible without departing from the scope of present invention.

According to a non-limiting exemplary embodiment of the present invention, the multiple buttons 204a and 204b are used for an initiation and a termination of the predefined test sequence selected using the test selector means 202. The button 204a assists in initiating the predefined test sequence. The predefined test sequence corresponds to a test sequence selected by using the test selector means 202. The button 204b assists in terminating the predefined test sequence.

According to a non-limiting exemplary embodiment of the present invention, the display means 206 displays a name corresponding to the predefined test sequence and a result generated corresponding to the predefined test sequence presented to the subject. The result is displayed onto the display means 206 as soon as the button 204b is pressed for termination of the predefined test sequence. The display means 206 preferably includes LCD monitor and the like.

According to a non-limiting exemplary embodiment of the present invention, the multiple indicating means 208a, 208b for indicating a result corresponding to the predefined test sequence and indicating the initiation and the termination of the predefined test sequence selected using the test selector means 202. The multiple indicating means 208a, 208b could preferably include but not limited to light emitting diodes (LEDs) and the like.

Figure 3:
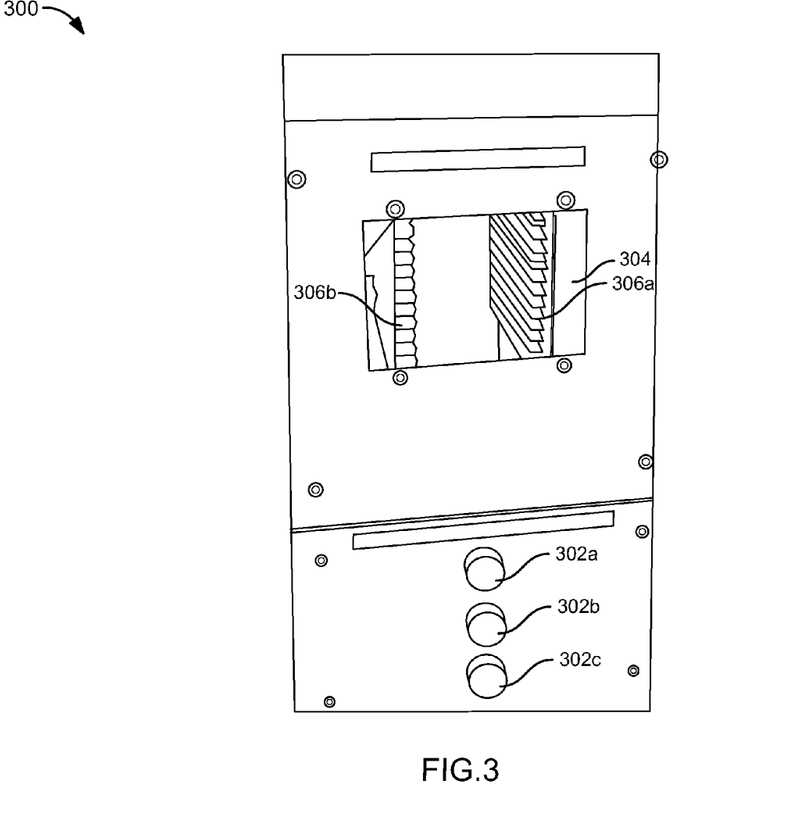
FIG. 3 is a diagram depicting a first test unit constructed in accordance with this invention.

Referring to FIG. 3 is a diagram 300 depicting a first test unit constructed in accordance with this invention. The first test unit 300 includes multiple light indicators 302a, 302b, and 302c for presenting the simple driving reaction test sequence and the complex reaction test sequence to the subject, a depth perception window 304 having a first lighting panel 306a and a second lighting panel 306b configured on either side for presenting the depth perception test sequence to the subject.

In accordance with a non-limiting exemplary embodiment of the present invention, the multiple light indicators 302a, 302b and 302c corresponds to multiple colors red, yellow and green respectively. The first test unit 300 presents the simple driving reaction test sequence and the complex reaction test sequence to the subject on selection of the first knob position and the second knob position respectively using the test selector means provided on the master control unit. The simple reaction test sequence causes the light indicator 302a and the light indicator 302c to glow and go off in a random manner prompting the subject to respond to the status of the light indicators 302a and 302c using the first switching module. The subject responds with an accelerator button upon visualizing glowing of light indicator 302c and responds with a brake button upon visualizing glowing of light indicator 302a. The response time taken by the subject is recorded using a timer means (not shown). The response time not exceeding 0.37 seconds qualifies the subject in the simple driving reaction test sequence and the corresponding result is displayed on the display means present in the master control unit.

The complex reaction test sequence involves an additional light indicator 302b increasing the complexity of the test sequence however the procedure for evaluating the competency of the subject remains the same except the subject needs to wait for responding to the status of the light indicator 302a and 302c. When the light indicator 302b glows the subject is required to wait for until the light indicators 302a, 302c changes there status and light indicator 302b goes off. The response time of the subject not exceeding 0.67 seconds qualifies the subject in the complex driving reaction test sequence. The light indicators 302a, 302b, 302c preferably include light lamps and the like.

In accordance with a non-limiting exemplary embodiment of the present invention, the depth perception window 304 includes a first lighting panel 306a and a second lighting panel 306b configured on either side. The first test unit 300 presents the depth perception test sequence to the subject on selection of the third knob position through the test selector means. The depth perception test sequence activates the first lighting panel 306a and the second lighting panel 306b configured on either side of the depth perception window 304. The first and second lighting panels 306a, 306b includes multiple lighting means preferably LEDs arranged in rows and columns. The depth perception test sequence prompts the subject to look into the depth perception window 304 and press an appropriate button from a set of buttons present in the second switching module keeping a column of lighting means corresponding to first lighting panel 306a fixed and a column of lighting means corresponding to second lighting panel 306b moving. The depth perception test sequence evaluates and determines competency of the subject with respect to a difference of distance between the column of lighting means which is fixed and the column of lighting means which appears to be moving. The difference of distance not exceeding 75 mm qualifies the subject in the depth perception test sequence.

Figure 4:
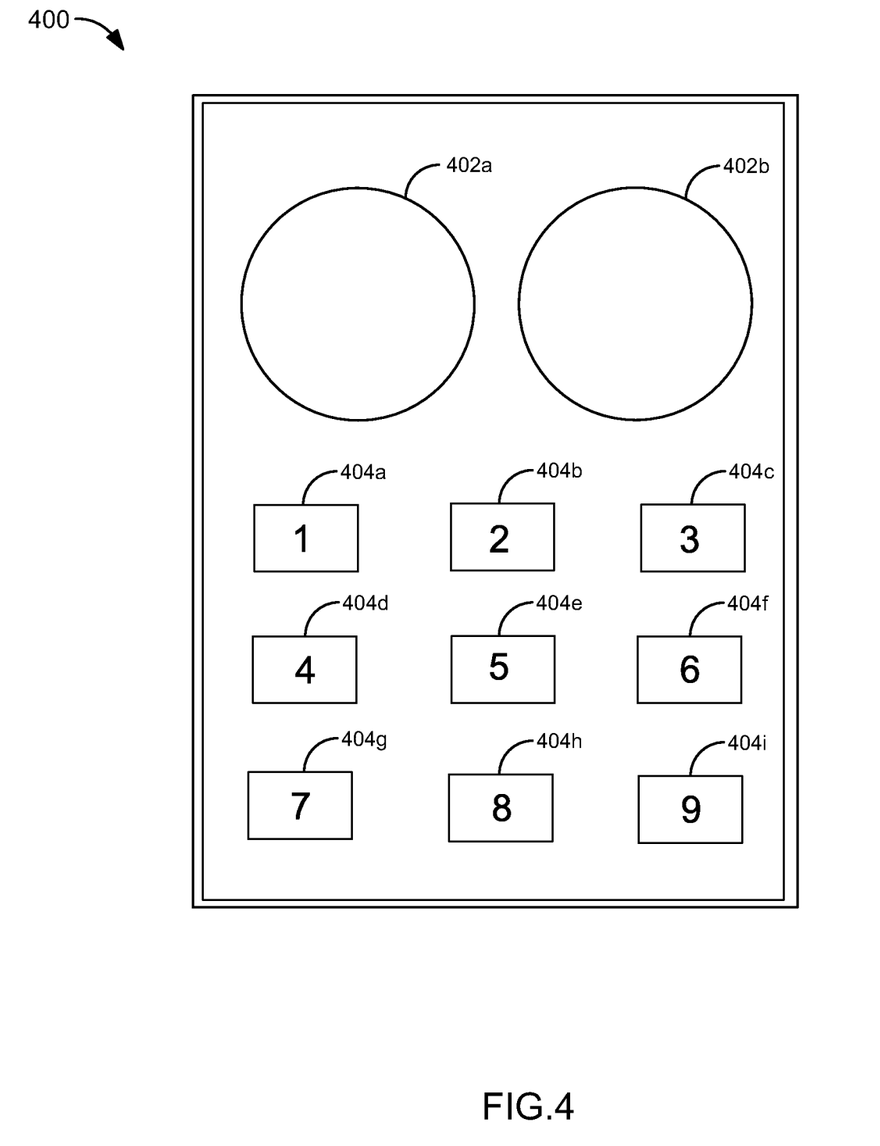
FIG. 4 is a diagram depicting a second test unit constructed in accordance with this invention.

Referring to FIG. 4 is a diagram 400 depicting a second test unit constructed in accordance with this invention. The second test unit 400 includes multiple headlamps 402a, 402b for presenting the glare recovery test sequence to the subject and multiple traffic symbols 404a, 404b, 404c, 404d, 404e, 404f, 404g, 404h, 404i for presenting the low illumination test sequence and the glare recovery test sequence to the user.

According to a non-limiting exemplary embodiment of the present invention, the multiple traffic symbols 404a, 404b, 404c, 404d, 404e, 404f, 404g, 404h, 404i are activated when the low illumination test sequence is selected using the fourth knob position through the test selector means. Under the low illumination test sequence the subject is prompted to recognize a lowly illuminated traffic symbol and respond with an appropriate button from a set of buttons corresponding to multiple traffic symbols in the second switching module. The response time taken by the subject is recorded using a timer means (not shown). The response time not exceeding 7 seconds qualifies the subject in the low illumination test sequence and the corresponding result is displayed on the display means. The low illumination test sequence evaluates and determines the competency of the subject to drive under low level of illumination.

According to a non-limiting exemplary embodiment of the present invention, the multiple headlamps 402a, 402b are activated upon selecting the glare recovery test sequence using the test selector means provided on the master control unit. Under the glare recovery test sequence multiple headlights 402a, 402b are projected onto the eyes of the subject for a predetermined of time preferably 5 seconds. Furthermore, the multiple traffic symbols 404a, 404b, 404c, 404d, 404e, 404f, 404g, 404h, 404i glows at random prompting the subject to recognize and respond to a glowing traffic symbol from the multiple traffic symbols 404a, 404b, 404c, 404d, 404e, 404f, 404g, 404h, 404i with the appropriate button from the set of buttons corresponding to multiple traffic symbols 404a, 404b, 404c, 404d, 404e, 404f, 404g, 404h, 404i in the second switching module. The response time taken by the subject is recorded using a timer means (not shown). The response time not exceeding 8 seconds qualifies the subject in the glare recovery test sequence and the corresponding result is displayed on the display means present in the master control unit.

Figure 5:
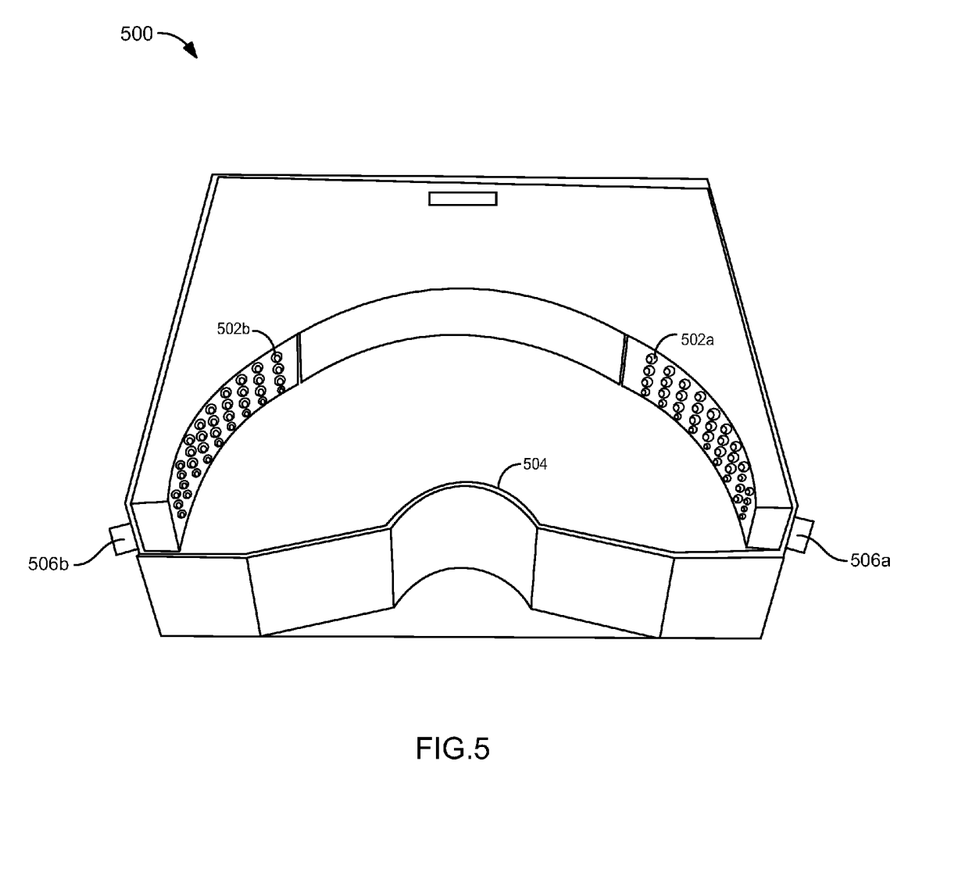
FIG. 5 is a diagram depicting a third test unit constructed in accordance with this invention.

Referring to FIG. 5 is a diagram 500 depicting a third test unit constructed in accordance with this invention. The third test unit 500 includes multiple lighting panels 502a, 502b configured on either edges of a platform, multiple switches 506a, and 506b on either side of the platform for generating a wave motion on either side of eyes of the subject, a predefined location 504 for the subject to place his/her chin in the center of the platform. The third test unit 500 presents the side vision test sequence to the subject upon selecting the side vision test sequence using the test selector means provided on the master control unit.

In accordance with a non-limiting exemplary embodiment of the present invention, the side vision test sequence prompts the subject to place his/her chin in the predefined location 504 in the center of the platform and look into the multiple glowing lighting panels 502a, 502b. The side vision test sequence further prompts the subject to press multiple switches 506a, and 506b causing the wave motion to move both sides of the subject's eyes. The side vision test sequence further prompts the subject to release the multiple switches 506a, and 506b as soon as the subject's eyes sights the wave motion into the multiple glowing lighting panels 502a, 502b. The total visualization angle subtended by the subject's eyes on either side is then calculated. The visualization angle subtended by both eyes of the subject equal to or exceeding 150 degrees, and the visualization angle equal to or exceeding 75 degrees in case of a single eye qualifies the subject in the side vision test sequence. The multiple lighting panels 502a, 502b includes multiple lighting means preferably LEDs arranged in multiple rows and columns.

Figure 6:
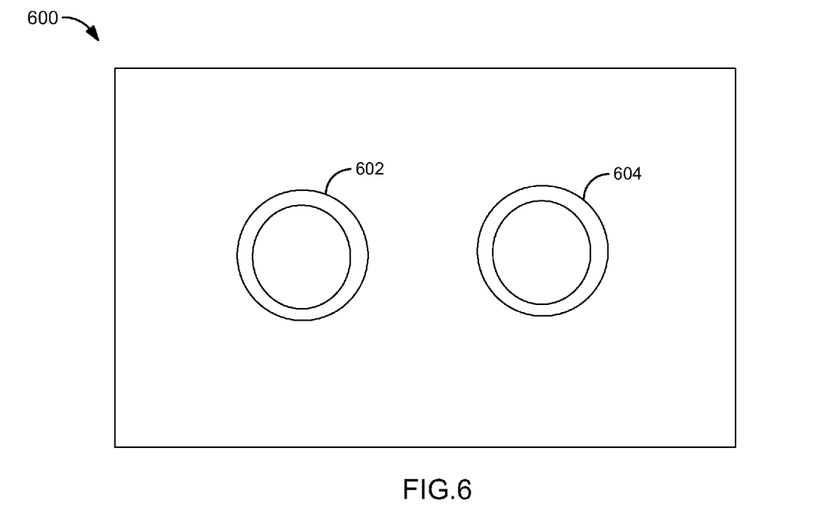
FIG. 6 is a diagram depicting a first switching module constructed in accordance with this invention.

Referring to FIG. 6 is a diagram 600 depicting a first switching module constructed in accordance with this invention. The first switching module 600 includes multiple switching elements 602 and 604 which enables the subject to convey the response corresponding to the simple driving reaction test sequence and the complex driving reaction test sequence as depicted in FIG. 3.

In accordance with a non-limiting exemplary embodiment of the present invention, the switching element 602 corresponds to an accelerator switch which is pressed by the subject upon visualizing an on status of green light indicator and the switching element 604 corresponds to a brake switch which is pressed by the subject upon visualizing an on status of red light indicator.

Figure 7:
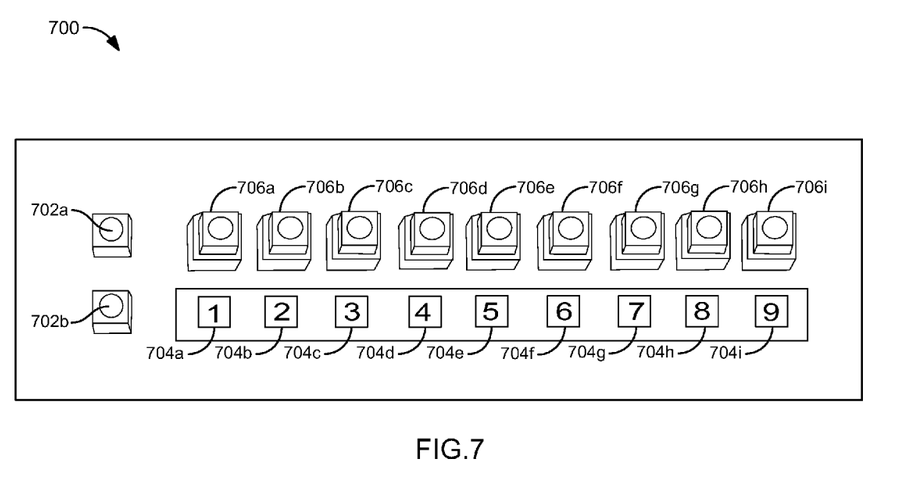
FIG. 7 is a diagram depicting a second switching module constructed in accordance with this invention.

Referring to FIG. 7 is a diagram 700 depicting a second switching module constructed in accordance with this invention. The second switching module 700 includes a first set of switching elements 706a, 706b, 706c, 706d, 706e, 706f, 706g, 706h, 706i corresponding to each of multiple traffic symbols 704a, 704b, 704c, 704d, 704e, 704f, 704g, 704h, 704i which enables the subject to respond to the low illumination vision test sequence and the glare recovery test sequence presented to the subject by the second test unit. The second switching module 700 further includes a second set of switching elements 702a, 702b which enables the subject to respond to the depth perception test sequence. The multiple second switching elements 702a, 702b corresponds to a forward button and a backward button respectively used for generating a wave motion which appears to be moving either from front to back or back to front as the subject keeps pressing the multiple second switching elements 702a, 702b under the exposure of the depth perception test sequence.

Figure 8:
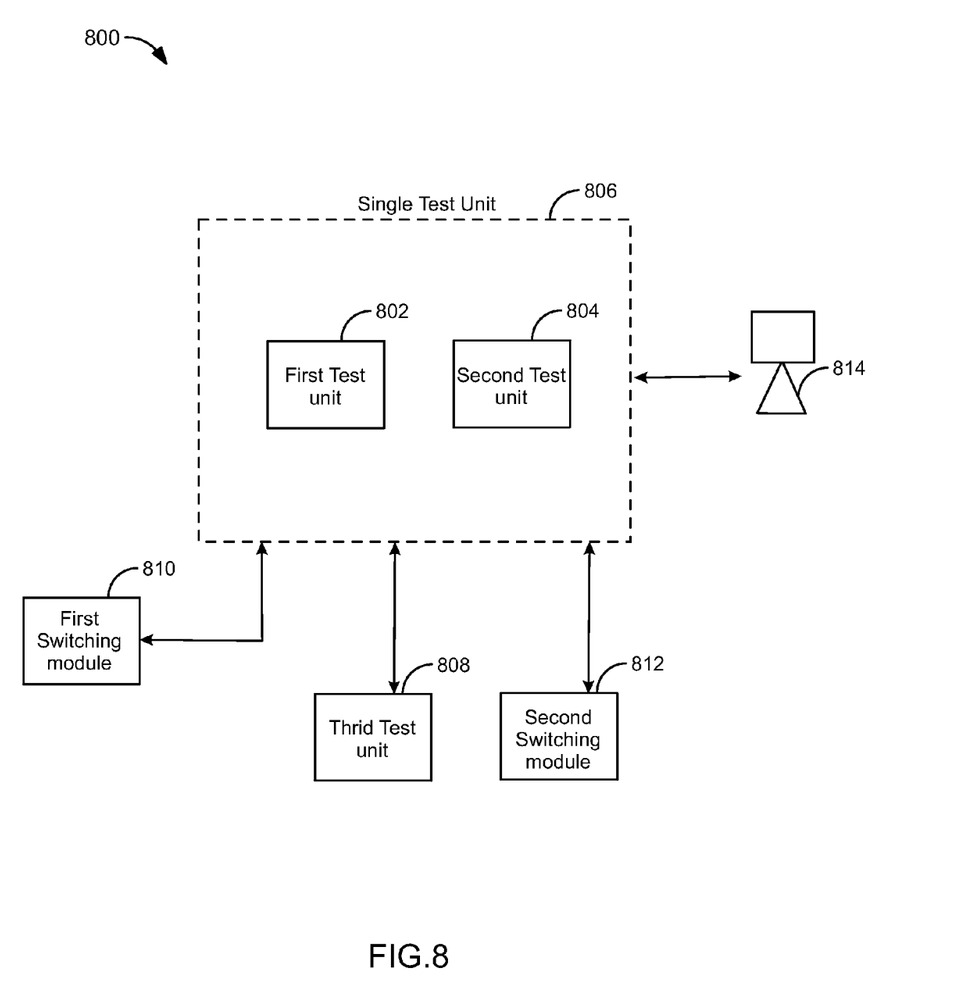
FIG. 8 is a block diagram depicting an overview of a system configured for testing and evaluating driving competency of a subject, according to an exemplary embodiment of the present invention.

Referring to FIG. 8 is a block diagram 800 depicting an overview of a system configured for testing and evaluating driving competency of a subject, according to an exemplary embodiment of the present invention. The system configured for testing and evaluating driving competency of the subject includes a first test unit 802 and a second test unit 804 configured as a single test unit 806, however for the person skilled in the art, without limiting the scope of the invention, it is equally possible to integrate or configure the first test unit 802, the second test unit 804 and a third test unit 808 as the single test unit 806. The system further includes a first switching module 810 and a second switching module 812 in communication with the first test unit 802 and the second test unit 804. Furthermore, a master control unit as depicted in FIG. 2 could be configured as an application platform in the form of a user interface on a communication device 814 communicatively coupled with the single test unit 806.

According to an exemplary embodiment of the present invention, the user interface present in the communication device 814 could be configured to display a plurality of information associated with the subject preferably including but not limited to a name associated with the subject, an image of the subject, a list of names associated with a predefined test sequences, a date and a time associated with the predefined test sequence, a time duration of the predefined test sequence, a result of the predefine test sequence presented to the subject, a reaction time and a deviation associated with the subject and the like. The predefined test sequences includes a simple driving reaction test sequence, a complex driving reaction test sequence, a depth perception test sequence, a low illumination vision test sequence, a glare recovery test sequence, and a side vision test sequence. The communication device 814 preferably includes a personal computer, a laptop, a PDA and the like.

According to an exemplary embodiment of the present invention, the application platform in the form of the user interface on the communication device 814 enables an instructor conducting the predefined test sequence for the subject to monitor and evaluate the results of the predefined test sequences instantly with greater ease. Furthermore, the application platform in the form of the user interface could also provide a provision for generating a test report associated with the subject and a provision for printing result of the predefined test sequence presented to the subject.

According to another exemplary embodiment the test units and switching modules of the invention can be devised or programmed for conducting specific tasks automatically under an application software for displaying, measuring, and recording a plurality of test parameters associated with testing and evaluating driving competency of the subject, as will be apparent to a person skilled in the art without limiting the scope of the invention.

While the present invention has been described with reference to one or more preferred embodiments, which embodiments have been set forth in considerable detail for the purposes of making a disclosure of the invention, such embodiments are merely exemplary and are not intended to be limiting or represent an exhaustive enumeration of all aspects of the invention.

What is claimed is:

1. A system for testing and evaluating driving competency of the subject, comprising:

a first test unit comprising a plurality of light indicators and a perception window comprising a first lighting panel and a second lighting panel configured on either side,
    wherein the first test unit is configured to provide a plurality of tests to the subject,
    wherein the plurality of tests comprise a simple driving reaction test, a complex driving reaction test, and a depth perception test,
    wherein the simple driving reaction test and complex driving reaction test are configured to test reaction time, such that a reaction time not exceeding a first predetermined time qualifies under the simple reaction test and a reaction time not exceeding a second predetermined time different than the first predetermined time qualifies under the complex reaction test,
    wherein the depth perception test is configured to evaluate the subject's ability to measure the distance between a column of lighting that appears fixed and a column of lighting that appears to be moving, wherein the depth perception test is satisfied when the difference of distance between the column of lighting which is fixed and the column of lighting that appears to be moving does not exceed a predetermined value;

a second test unit comprising a plurality of headlamps,
    wherein the second test unit is configured to provide a plurality of second driving tests to the subject,
    wherein the plurality of second driving tests comprise a low illumination vision test, and a glare recovery test,
    wherein the low illumination vision test is configured to determine the subject's ability to timely recognize multiple traffic symbols under a low level of illumination, such that a recognition time not exceeding a predetermined time is a qualifying recognition time,
    wherein the glare recovery test is configured to determine a subject's ability to timely recover from a glare effect caused by an approaching vehicle, such that a recovery time not exceeding a predetermined time is a qualifying recovery time;

a third test unit comprising a plurality of lighting panels configured on either edges of a platform, a plurality of switches on either side of the platform to generate a wave motion on either side of the subject's eyes; and a predefined location for placing a chin of the subject on the center of the platform,
    wherein the third test unit is configured to provide a third driving test to the subject,
    wherein the third driving test comprises a side vision test,
    wherein the side vision test is configured to determine the subject's angle of vision on either side of a path, such that an angle of vision equal to or exceeding a predetermined angle is a qualifying angle of vision;

a first switching module comprising a first plurality of switching elements in communication with the first test unit,
    wherein the first switching module is configured to register the subject's response in the simple driving reaction test and the complex driving reaction test,
    wherein the first switching module further comprises a first set of input receiving means, wherein the first set of input receiving means comprises an accelerator and a brake,
    wherein the first set of input receiving means allows the subject to register responses to the simple and complex reaction tests;

a second switching module comprising a second plurality of switching elements in communication with the first test unit and the second test unit,
    wherein the second switching module is configured to register the subject's response in the low illumination vision test, the glare recovery test and the depth perception test,
    wherein the second switching module comprises a second set of input receiving means,
    wherein the first set of input receiving means is used to provide input for the depth perception test, and the second set of input receiving means correspond to a plurality of traffic symbols,
    wherein the second set of input receiving means is used to provide input for the low illumination test and glare recovery test; and a master control unit comprising a test selector, a display, a plurality of buttons, and a plurality of indicators,
    wherein the test selector is for selecting one of the first, second and third driving tests,
    wherein the display is for displaying a name and a result corresponding to at least one of the first, second and third driving test,
    wherein the plurality of buttons is for performing an initiation and a termination of the first, second and third driving test,
    wherein the plurality of indicators are for indicating a result, an initiation, and a termination of the first, second, and third driving test,
    wherein the master control unit is configured to interact and control the first test unit, the second test unit, the third test unit, the first switching module, and the second switching module,
    wherein the master control unit, the first test unit, the second test unit, the third test unit, the first switching module, and the second switching module may be programmed to display, measure, and record a plurality of test parameters associated with testing and evaluating driving competency of the subject.

2. The system of claim 1 wherein the simple driving reaction test and the complex driving reaction test are capable of evaluating and determining an alertness level of the subject based on a response time of the subject.

3. The system of claim 2, wherein the qualifying response time in the simple driving reaction test sequence for the subject, is not more than 0.37 seconds.

4. The system of claim 2, wherein the qualifying response time in the complex driving reaction test sequence for the subject is not more than 0.67 seconds.

5. The system of claim 1, wherein the predetermined distance in the depth perception test is 75 mm.

6. The system of claim 1, wherein the qualifying response time for the subject in the low illumination vision test sequence is not more than 7 seconds.

7. The system of claim 1, wherein the response time for the subject in the glare recovery test sequence is not more than 8 seconds.

8. The system of claim 1, wherein the qualifying visualization angle for the subject in the side vision test sequence is equal to or more than 150 degrees.

9. The system of claim 1 further comprising a timer to record the response time taken by the subject.

10. The system of claim 1, further comprising an application platform in the form of a user interface on a communication device including: a personal computer, a laptop, and a PDA, which is communicatively coupled to the first test unit, the second test unit, and the third test unit.

11. The system of claim 10, wherein the application platform, in the form of user interface on the communication device enables an instructor to administer at least one of said tests, monitor and evaluate the results of the test, and generate a test report associated with the subject.

* * * * *